United States Patent [19]
Hosoda et al.

[11] Patent Number: 5,767,318
[45] Date of Patent: Jun. 16, 1998

[54] PROCESS FOR PRODUCING A HIGH PURITY 2,4'-DIHYDROXYDIPHENYLSULFONE

[75] Inventors: Masaaki Hosoda; Masahiro Makino, both of Sabae, Japan

[73] Assignee: Nicca Chemical Co., Ltd., Fukui-ken, Japan

[21] Appl. No.: 586,313

[22] Filed: Jan. 17, 1996

[30] Foreign Application Priority Data

Jul. 25, 1995 [JP] Japan ................... 7-209200

[51] Int. Cl.$^6$ ..................... C07C 315/06
[52] U.S. Cl. ........................... 568/33
[58] Field of Search ................. 568/33

[56] References Cited

U.S. PATENT DOCUMENTS

| | | |
|---|---|---|
| 2,392,137 | 1/1946 | Foster . |
| 5,001,270 | 3/1991 | Zemlanicky et al. . |
| 5,097,074 | 3/1992 | Ogata et al. . |
| 5,378,674 | 1/1995 | Kobayashi et al. . |

FOREIGN PATENT DOCUMENTS

| | | |
|---|---|---|
| 0 326 320 | 1/1989 | European Pat. Off. . |

*Primary Examiner*—Alan L. Rotman
*Assistant Examiner*—Jean F. Vollano
*Attorney, Agent, or Firm*—Millen, White, Zelano & Branigan, P.C.

[57] ABSTRACT

A process for producing a high purity 2,4'-dihydroxydiphenylsulfone (2,4'-isomer) comprising separating 2,4'-isomer from 4,4'-dihydroxydiphenylsulfone (4,4'-isomer) by adding a hydroxide of an alkali metal in an amount which is the total of an amount by mol 1.6 to 2.2 times as great as the amount by mol of 2,4'-isomer and an amount by mol 0.8 to 1.2 times as great as the amount by mol of 4,4'-isomer to a solution of a mixture of 2,4'-isomer and 4,4'-isomer containing 15% by weight or more of 2,4'-isomer in water, to allow 2,4'-isomer to remain dissolved in water in the form of a dialkali metal salt thereof and 4,4'-isomer to be precipitated from the solution in the form of a monoalkali metal salt thereof. A carbonate of an alkali metal may also be used. In order to accelerate the operation, an excess amount of the alkali may be added, which is subsequently neutralized. A high purity 2,4'-isomer having a purity of 95 to 99.5% by weight can be obtained easily with a high yield from a mixture of the isomers containing 15% by weight or more of 2,4'-isomer.

20 Claims, No Drawings

PROCESS FOR PRODUCING A HIGH PURITY 2,4-DIHYDROXYDIPHENYLSULFONE

FIELD OF THE INVENTION

The present invention relates to a process for producing a high purity 2,4'-dihydroxydiphenylsulfone. More particularly, the present invention relates to a process for efficiently producing a high purity 2,4'-dihydroxydiphenylsulfone which is useful as a developer for heat sensitive recording paper and the like by removing 4,4'-dihydroxydiphenylsulfone from a mixture of 2,4'-dihydroxydiphenylsulfone and 4,4'-dihydroxydiphenylsulfone.

PRIOR ART OF THE INVENTION

Dihydroxydiphenylsulfone which is prepared by the reaction of phenol and sulfuric acid or the like is generally obtained in the form of a mixture of two isomers which are 4,4'-dihydroxydiphenylsulfone and 2,4'-dihydroxydiphenylsulfone, and the mixture generally contains 4,4'-dihydroxydiphenylsulfone in a large amount and 2,4'-dihydroxy-diphenylsulfone in a small amount. Among these isomers, 4,4'-dihydroxydiphenylsulfone is widely used as a component of engineering plastics and a coupler for color photography as well as a developer for heat sensitive recording paper.

On the other hand, 2,4'-dihydroxydiphenylsulfone has not been widely utilized even though it has properties as a developer for heat sensitive recording paper superior to 4,4'-dihydroxydiphenylsulfone because the amount produced by the reaction of phenol and a sulfonating agent such as sulfuric acid is rather small, and also because physical and chemical properties of 2,4'-dihydroxydiphenylsulfone and 4,4'-dihydroxydiphenylsulfone are similar to each other and isolation and purification of 2,4'-dihydroxydiphenylsulfone is difficult. The present inventors disclosed a process for producing 2,4'-dihydroxydiphenyl-sulfone by the reaction of phenyl and sulfuric acid with a high selectivity (Japanese Patent Application Laid-Open No. Heisei 6(1994)-107622. However, production of 2,4'-dihydroxydiphenylsulfone having a higher purity is increasingly desired.

SUMMARY OF THE INVENTION

The present invention accordingly has as an object the provision of a process for efficiently producing a high purity 2,4'-dihydroxydiphenyl-sulfone which is useful as a developer for heat sensitive recording paper and the like by removing 4,4'-dihydroxydiphenylsulfone from a mixture of 2,4'-dihydroxydiphenylsulfone and 4,4'-dihydroxydiphenylsulfone.

Extensive investigations undertaken by the present inventors with the object described above lead to a discovery that 2,4'-dihydroxydiphenylsulfone can be efficiently separated from 4,4'-dihydroxydiphenylsulfone in a mixture thereof by selectively forming a dialkali metal salt of 2,4'-dihydroxydiphenylsulfone. The present invention has been completed on the basis of the discovery.

Thus, the present invention provides the following processes: (1) A process for producing a high purity 2,4'-dihydroxydiphenylsulfone comprising separating 2,4'-dihydroxydiphenylsulfone from 4,4'-dihydroxydiphenylsulfone by adding a hydroxide of an alkali metal in an amount which is the total of an amount by mol 1.6 to 2.2 times as great as the amount by mol of 2,4'-dihydroxydiphenylsulfone and an amount by mol 0.8 to 1.2 times as great as the amount by mol of 4,4'-dihydroxydiphenylsulfone to a solution of a mixture of 2,4'-dihydroxydiphenylsulfone and 4,4'-dihydroxydiphenylsulfone containing 15% by weight or more of 2,4'-dihydroxydiphenylsulfone in water, to allow 2,4'-dihydroxydiphenylsulfone to remain dissolved in water in the form of a dialkali metal salt thereof and 4,4'-dihydroxydiphenylsulfone to be precipitated from the solution in the form of a monoalkali metal salt thereof. (2) A process for producing a high purity 2,4'-dihydroxydiphenylsulfone according to (1) described above, wherein 2,4'-dihydroxydiphenylsulfone is separated from 4,4'-dihydroxydiphenylsulfone by adding a hydroxide of an alkali metal in an amount which is the total of an amount by mol 1.6 to 2.2 times as great as the amount by mol of 2,4'-dihydroxydiphenylsulfone and an amount by mol 1.6 to 2.4 times as great as the amount by mol of 4,4'-dihydroxydiphenylsulfone to a solution of a mixture of 2,4'-dihydroxydiphenylsulfone and 4,4'-dihydroxydiphenylsulfone containing 15% by weight or more of 2,4'-dihydroxydiphenylsulfone in water, and by subsequently adding an acid in an amount by mol corresponding to an amount by mol of the hydroxide of an alkali metal which is 0.8 to 1.2 times as great as the amount by mol of 4,4'-dihydroxydiphenylsulfone to the resultant solution to neutralize the alkali. (3) A process for producing a high purity 2,4'-dihydroxydiphenylsulfone comprising separating 2,4'-dihydroxydiphenylsulfone from 4,4'-dihydroxydiphenylsulfone by adding a carbonate of an alkali metal in an amount which is the total of an amount by mol 0.8 to 1.1 times as great as the amount by mol of 2,4'-dihydroxydiphenylsulfone and an amount by mol 0.4 to 0.6 times as great as the amount by mol of 4,4'-dihydroxydiphenylsulfone to a solution of a mixture of 2,4'-dihydroxydiphenylsulfone and 4,4'-dihydroxydiphenylsulfone containing 15% by weight or more of 2,4'-dihydroxydiphenylsulfone in water, to allow 2,4'-dihydroxydiphenylsulfone to remain dissolved in water in the form of a dialkali metal salt thereof and 4,4'-dihydroxydiphenylsulfone to be precipitated from the solution in the form of a monoalkali metal salt thereof. (4) A process for producing a high purity 2,4'-dihydroxydiphenylsulfone according to (3) described above, wherein 2,4'-dihydroxydiphenylsulfone is separated from 4,4'-dihydroxydiphenylsulfone by adding a carbonate of an alkali metal in an amount which is the total of an amount by mol 0.8 to 1.1 times as great as the amount by mol of 2,4'-dihydroxydiphenylsulfone and an amount by mol 0.8 to 1.2 times as great as the amount by mol of 4,4'-dihydroxydiphenylsulfone to a solution of a mixture of 2,4'-dihydroxydiphenylsulfone and 4,4'-dihydroxydiphenylsulfone containing 15% by weight or more of 2,4'-dihydroxydiphenylsulfone in water, and by subsequently adding an acid in an amount by mol corresponding to an amount by mol of the carbonate of an alkali metal which is 0.4 to 0.6 times as great as the amount by mol of 4,4'-dihydroxydiphenylsulfone to the resultant solution to neutralize the alkali. (5) A process for producing a high purity 2,4'-dihydroxydiphenylsulfone according to any one of (1) to (4) described above, wherein the monoalkali metal salt of 4,4'-dihydroxydiphenylsulfone which is precipitated from the solution is removed by filtration at 20° to 70° C. (6) A process for producing a high purity 2,4'-dihydroxydiphenylsulfone according to (5) described above, wherein 2,4'-dihydroxydiphenylsulfone is precipitated from a filtrate obtained by the filtration by adjusting pH of the filtrate to 4 to 6 with addition of an acid. (7) A process for producing a high purity 2,4'-dihydroxydiphenylsulfone according to (5) described above, wherein a monoalkali metal salt of 2,4'-dihydroxydiphenylsulfone is precipitated from a filtrate obtained by the filtration by adjusting pH of the filtrate to 6 to 10.5, isolated, and subsequently dissolved in an aqueous solvent, and 2,4'-dihydroxy-diphenylsulfone is precipitated from the resultant aqueous solution by adjusting pH of the aqueous solution to 4 to 6 with addition of an acid. (8) A process for producing a high purity 2,4'-dihydroxydiphenylsulfone according to (5), wherein an aliphatic alcohol having 1 to 3 carbon atoms is added to a filtrate obtained by the filtration in such an amount that the resultant mixed solvent contains 60 to 90% by weight of water and 40 to 10% by weight of the aliphatic alcohol, and 2,4'-dihydroxydiphenylsulfone is precipitated from the resultant solution by adjusting pH of the solution to 4 to 6 with addition of an acid.

The preferred embodiments of the present invention include the following: (9) A process for producing a high purity 2,4'-dihydroxydiphenylsulfone comprising separating 2,4'-dihydroxydiphenylsulfone from 4,4'-dihydroxydiphenylsulfone by adding a hydroxide of an alkaline earth metal in an amount which is the total of an amount by mol 0.8 to 1.1 times as great as the amount by mol of 2,4'-dihydroxydiphenylsulfone and an amount by mol 0.4 to 0.6 times as great as the amount by mol of 4,4'-dihydroxydiphenylsulfone to a solution of a mixture of 2,4'-dihydroxydiphenylsulfone and 4,4'-dihydroxydiphenylsulfone containing 15% by weight or more of 2,4'-dihydroxydiphenylsulfone in water, to allow 2,4'-dihydroxydiphenylsulfone to remain dissolved in water by forming salts with two hydroxyl groups thereof and 4,4'-dihydroxy-diphenylsulfone to be precipitated from the solution by forming a salt with one of the hydroxyl groups thereof. (10) A process for producing a high purity 2,4'-dihydroxydiphenylsulfone comprising separating 2,4'-dihydroxydiphenylsulfone from 4,4'-dihydroxydiphenylsulfone by adding a hydroxide of an alkaline earth metal in an amount which is the total of an amount by mol 0.8 to 1.1 times as great as the amount by mol of 2,4'-dihydroxydiphenylsulfone and an amount by mol 0.8 to 1.2 times as great as the amount by mol of 4,4'-dihydroxydiphenylsulfone to a solution of a mixture of 2,4'-dihydroxydiphenylsulfone and 4,4'-dihydroxydiphenylsulfone containing 15% by weight or more of 2,4'-dihydroxydiphenylsulfone in water, and by subsequently adding an acid to the resultant solution to neutralize the alkali in an amount by mol corresponding to an amount by mol of the hydroxide of an alkaline earth metal which is 0.4 to 0.6 times as great as the amount by mol of 4,4'-dihydroxydiphenylsulfone, to allow 2,4'-dihydroxydiphenylsulfone to remain dissolved in water by forming salts with two hydroxyl groups thereof and 4,4'-dihydroxydiphenylsulfone to be precipitated from the solution by forming a salt with one of the hydroxyl groups thereof. (11) A process for producing a high purity 2,4'-dihydroxydiphenylsulfone according to any one of (1) to (10) described above, wherein the amount by weight of water used as the solvent is 0.5 to 5.0 times as great as the total of the amounts by weight of 2,4'-dihydroxydiphenylsulfone and 4,4'-dihydroxydiphenylsulfone.

Other and further objects, features and advantages of the invention will appear more fully from the following description.

DETAILED DESCRIPTION OF THE INVENTION

In the process of the present invention, a mixture of 2,4'-dihydroxydiphenylsulfone and 4,4'-dihydroxydiphenylsulfone which contains 15% by weight or more of 2,4'-dihydroxydiphenylsulfone is used. Dihydroxydiphenylsulfone can be produced by mixing phenol with sulfuric acid, heating the mixture, and removing water formed by the reaction as an azeotropic mixture with phenol. It is preferred that the reaction is conducted under a reduced pressure. An additional amount of phenol may be added to the reaction system during the reaction to compensate the amount of phenol lost by the azeotropic distillation with water. A compound which is distilled by forming an azeotrope with water, such as toluene, chlorobenzene, xylene, or the like, may be used in addition to phenol and sulfuric acid to accelerate distillation of water by forming an azeotrope.

In the present invention, when the content of 2,4'-dihydroxydiphenylsulfone in a mixture of the isomers of dihydroxy-diphenylsulfone is less than 15% by weight, the operation of separation must be conducted repeatedly in order to obtain a high purity 2,4'-dihydroxydiphenylsulfone. This causes increase in the time for the operation and decrease in the yield of the resultant high purity 2,4'-dihydroxydiphenylsulfone. Therefore, a content less than 15% by weight is not preferred. When a phosphorus compound, such as phosphonic acid, phosphinic acid, phosphoric acid, or the like, is present in the reaction system of phenol and sulfuric acid, the content of 2,4'-dihydroxydiphenylsulfone in the resultant mixture of the isomers of dihydroxydiphenylsulfone can be increased.

In the process of the present invention, a hydroxide of an alkali metal in an amount which is the total of an amount by mol 1.6 to 2.2 times as great as the amount by mol of 2,4'-dihydroxydiphenylsulfone and an amount by mol 0.8 to 1.2 times as great as the amount by mol of 4,4'-dihydroxydiphenylsulfone can be added to a solution of a mixture of 2,4'-dihydroxydiphenylsulfone and 4,4'-dihydroxydiphenylsulfone in water. The hydroxide of an alkali metal is not particularly limited, and lithium hydroxide, sodium hydroxide, potassium hydroxide, or the like, may be used. Among them, sodium hydroxide is preferably used.

In the process of the present invention, a hydroxide of an alkali metal in an amount which is the total of an amount by mol 1.6 to 2.2 times as great as the amount by mol of 2,4'-dihydroxydiphenylsulfone and an amount by mol 1.6 to 2.4 times as great as the amount by mol of 4,4'-dihydroxydiphenylsulfone may also be added to a solution of a mixture of 2,4'-dihydroxydiphenylsulfone and 4,4'-dihydroxydiphenylsulfone in water. Then, an acid in an amount by mol corresponding to an amount by mol of the hydroxide of an alkali metal which is 0.8 to 1.2 times as great as the amount by mol of 2,4'-dihydroxydiphenylsulfone is added to neutralize the alkali. When a hydroxide of an alkali metal in an amount by mol which is the total of an amount by mol 1.6 to 2.2 times as great as the amount by mol of 2,4'-dihydroxydiphenylsulfone and an amount by mol 1.6 to 2.4 times as great as the amount by mol of 4,4'-dihydroxydiphenylsulfone is added to a solution of a mixture of 2,4'-dihydroxydiphenylsulfone and 4,4'-dihydroxydiphenylsulfone in water, the dihydroxydiphenylsulfones are quickly dissolved into water in the form of a dialkali metal salt thereof. Therefore, the time for the operation can be decreased, and the purity of the resultant 2,4'-dihydroxydiphenylsulfone can be increased. The acid used for the neutralization is not particularly limited, and an inorganic acid, such as hydrochloric acid, sulfuric acid, phosphoric acid, or the like, or an organic acid, such as formic acid, acetic acid, propionic acid, or the like, may be used. When an excess amount of an alkali is neutralized with an acid, the salt formed by the neutralization works as an agent for salting out.

In the process of the present invention, when the amount of the hydroxide of an alkali metal present in the solution of a mixture of 2,4'-dihydroxydiphenylsulfone and 4,4'-dihydroxydiphenylsulfone in water is adjusted to an amount which is the total of an amount by mol 1.6 to 2.2 times as great as the amount by mol of 2,4'-dihydroxydiphenylsulfone and an amount by mol 0.8 to 1.2 times as great as the amount by mol of 4,4'-dihydroxydiphenylsulfone, 2,4'-dihydroxydiphenylsulfone is substantially converted into a dialkali metal salt thereof, and 4,4'-dihydroxydiphenylsulfone is substantially converted into a monoalkali metal salt thereof. The dialkali metal salt of 2,4'-dihydroxydiphenyl-sulfone has a greater solubility in water used as the solvent than that of the monoalkali metal salt of 4,4'-dihydroxydiphenylsulfone. By taking advantage of the difference in the solubilities of the two compounds, it can be achieved that the dialkali metal salt of 2,4'-dihydroxydiphenylsulfone remains dissolved in water and the monoalkali metal salt of 4,4'-dihydroxydiphenylsulfone is precipitated from the solution.

In the process of the present invention, when the amount of the hydroxide of an alkali metal present in the solution is less than the amount which is the total of an amount by mol 1.6 times as great as the amount by mol of 2,4'-dihydroxydiphenylsulfone and an amount by mol 0.8 times as great as the amount by mol of 4,4'-dihydroxydiphenylsulfone, there is the possibility that the purity of the resultant 2,4'-dihydroxydiphenylsulfone decreases. When the amount of the hydroxide of an alkali metal present in the solution is more than the amount which is the total of an amount by mol 2.2 times as great as the amount by mol of 2,4'-dihydroxydiphenylsulfone and an amount by mol 1.2 times as great as the amount by mol of 4,4'-dihydroxydiphenylsulfone, there is the possibility that the yield of the resultant high purity 2,4'-dihydroxydiphenylsulfone decreases.

In the process of the present invention, a carbonate of an alkali metal in an amount which is the total of an amount by mol 0.8 to 1.1 times as great as the amount by mol of 2,4'-dihydroxydiphenylsulfone and an amount by mol 0.4 to 0.6 times as great as the amount by mol of 4,4'-dihydroxydiphenylsulfone can also be added to a solution of a mixture of 2,4'-dihydroxydiphenylsulfone and 4,4'-dihydroxydiphenyl-sulfone in water. The carbonate of an alkali metal is not particularly limited, and lithium carbonate, sodium carbonate, potassium carbonate, or the like, may be used. Among them, sodium carbonate is preferably used.

In the process of the present invention, a carbonate of an alkali metal in an amount which is the total of an amount by mol 0.8 to 1.1 times as great as the amount by mol of 2,4'-dihydroxydiphenylsulfone and an amount by mol 0.8 to 1.2 times as great as the amount by mol of 4,4'-dihydroxydiphenylsulfone may also be added to a solution of a mixture of 2,4'-dihydroxydiphenylsulfone and 4,4'-dihydroxydiphenylsulfone in water. Then, an acid in an amount by mol corresponding to an amount by mol of the carbonate of an alkali metal which is 0.4 to 0.6 times as great as the amount by mol of 2,4'-dihydroxydiphenylsulfone is added to neutralize the alkali. When a carbonate of an alkali metal in an amount by mol which is the total of an amount by mol 0.8 to 1.1 times as great as the amount by mol of 2,4'-dihydroxydiphenylsulfone and an amount by mol 0.8 to 1.2 times as great as the amount by mol of 4,4'-dihydroxydiphenylsulfone is added to a solution of a mixture of 2,4'-dihydroxydiphenylsulfone and 4,4'-dihydroxydiphenylsulfone in water, the dihydroxydiphenylsulfones are quickly dissolved into water by forming dialkali metal salts thereof. Therefore, the time for the operation can be decreased, and the purity of the resultant 2,4'-dihydroxydiphenylsulfone can be increased. The acid used for the neutralization is not particularly limited, and an inorganic acid, such as hydrochloric acid, sulfuric acid, phosphoric acid, or the like, or an organic acid, such as formic acid, acetic acid, propionic acid, or the like, may be used. When an excess amount of an alkali is neutralized with an acid, the salt formed by the neutralization works as an agent for salting out.

In the process of the present invention, when the amount of the carbonate of an alkali metal present in the solution of a mixture of 2,4'-dihydroxydiphenylsulfone and 4,4'-dihydroxydiphenylsulfone in water is adjusted to an amount which is the total of an amount by mol 0.8 to 1.1 times as great as the amount by mol of 2,4'-dihydroxydiphenylsulfone and an amount by mol 0.4 to 0.6 times as great as the amount by mol of 4,4'-dihydroxydiphenylsulfone, 2,4'-dihydroxydiphenylsulfone is substantially converted into a dialkali metal salt thereof, and 4,4'-dihydroxydiphenylsulfone is substantially converted into a monoalkali metal salt thereof. The dialkali metal salt of 2,4'-dihydroxydiphenylsulfone has a greater solubility in water used as the solvent than that of the monoalkali metal salt of 4,4'-dihydroxydiphenylsulfone. By taking advantage of the difference in the solubilities of the two compounds, it can be achieved that the dialkali metal salt of 2,4'-dihydroxy-diphenylsulfone remains dissolved in water and the monoalkali metal salt of 4,4'-dihydroxydiphenylsulfone is precipitated from the solution.

In the process of the present invention, when the amount of the carbonate of an alkali metal present in the solution is less than the amount which is the total of an amount by mol 0.8 times as great as the amount by mol of 2,4'-dihydroxydiphenylsulfone and an amount by mol 0.4 times as great as the amount by mol of 4,4'-dihydroxydiphenylsulfone, there is the possibility that the purity of the resultant 2,4'-dihydroxydiphenylsulfone decreases. When the amount of the carbonate of an alkali metal present in the solution is more than the amount which is the total of an amount by mol 1.1 times as great as the amount by mol of 2,4'-dihydroxydiphenylsulfone and an amount by mol 0.6 times as great as the amount by mol of 4,4'-dihydroxydiphenylsulfone, there is the possibility that the yield of the resultant high purity 2,4'-dihydroxydiphenylsulfone decreases.

In the process of the present invention, a hydroxide of an alkaline earth metal can be used in place of a hydroxide of an alkali metal or a carbonate of an alkali metal. When a hydroxide of an alkaline earth metal is used, the hydroxide of an alkaline earth metal in an amount which is the total of an amount by mol 0.8 to 1.1 times as great as the amount by mol of 2,4'-dihydroxydiphenylsulfone and an amount by mol 0.4 to 0.6 times as great as the amount by mol of 4,4'-dihydroxydiphenylsulfone can be added to a solution of a mixture of 2,4'-dihydroxydiphenylsulfone and 4,4'-dihydroxydiphenylsulfone in water. A process in which a hydroxide of an alkaline earth metal is added in an excess amount and subsequently neutralized with an acid may be conducted as well.

In the process of the present invention, the method of achieving the condition in which a dialkali metal salt of 2,4'-dihydroxydiphenylsulfone remains dissolved in water and a monoalkali metal salt of 4,4'-dihydroxydiphenylsulfone is precipitated from a solution is not particularly limited. For example, a monoalkali metal salt of 4,4'-dihydroxydiphenylsulfone can be allowed to be precipitated selectively by adjusting the amount or temperature of a solution containing a mixture of the dihydroxydiphenylsulfone isomers, or by adding a salt to a solution containing the mixture for salting out.

When the method of adjusting the temperature of the solution is used, the preferred temperature is different depending upon the type of the used alkali metal, the concentrations of 2,4'-dihydroxydiphenylsulfone and 4,4'-dihydroxydiphenylsulfone, the desired purity of 2,4'-dihydroxydiphenylsulfone, and the like factors. When the temperature is kept generally at 20° to 70° C., preferably at 30 to 50° C., the condition in which the dialkali metal salt of 2,4'-dihydroxydiphenylsulfone remains dissolved in water and the monoalkali metal salt of 4,4'-dihydroxydiphenylsulfone is precipitated from the solution can be realized. When the temperature is lower than 20° C., there is the possibility that the yield of the resultant high purity 2,4'-dihydroxydiphenylsulfone decreases because of precipitation of the dialkali salt of 2,4'-dihydroxydiphenylsulfone. When the temperature is higher than 70° C., there is the possibility that a part of the monoalkali metal salt remain dissolved in water, and the purity of the resultant 2,4'-dihydroxydiphenylsulfone decreases.

When the method of salting out is used, the salt used in the method is not particularly limited, and for example, lithium sulfate, sodium sulfate, potassium sulfate, magnesium sulfate, lithium chloride, sodium chloride, potassium chloride, magnesium chloride, calcium chloride, barium chloride, or the like, can be used.

In the process of the present invention, the method of separation of the monoalkali salt of 4,4'-dihydroxydiphenylsulfone which has been precipitated from the solution by adjustment of the temperature or by salting out is not particularly limited, and filtration, centrifugal separation, or the like method, can be used. In the process of the present invention, the monoalkali metal salt of 4,4'-dihydroxydiphenylsulfone remaining in the solution can be removed more completely when the monoalkali metal salt of 4,4'-dihydroxydiphenylsulfone precipitated by adjustment of the temperature is separated by a method like filtration, and the solution is subsequently treated with salting out.

In the process of the present invention, water as the solvent is used preferably in an amount by weight 0.5 to 5.0 times as great as the total of the amounts by weight of 2,4'-dihydroxydiphenylsulfone and 4,4'-dihydroxydiphenylsulfone, more preferably in an amount by weight of 0.8 to 3 times as great as the total of the amounts by weight of 2,4'-dihydroxydiphenylsulfone and 4,4'-dihydroxydiphenylsulfone. When the amount by weight of water used as the solvent is less than 0.5 times as great as the total of the amounts by weight of 2,4'-dihydroxydiphenylsulfone and 4,4'-dihydroxydiphenylsulfone, there is the possibility that the operability is inferior because of an excessively high concentration of the mixture for the treatment, and the separation of 2,4'-dihydroxydiphenylsulfone is adversely affected. When the amount by weight of water used as the solvent is more than 5.0 times as great as the total of the amounts by weight of 2,4'-dihydroxydiphenylsulfone and 4,4'-dihydroxydiphenylsulfone, there is the possibility that the purity of the resultant 2,4'-dihydroxydiphenylsulfone decreases because components other than 2,4'-dihydroxydiphenylsulfone remain in the solution in greater amounts.

In the process of the present invention, after the monoalkali salt of 4,4'-dihydroxydiphenylsulfone is separated and removed, the dialkali metal salt of 2,4'-dihydroxydiphenylsulfone in the solution is converted to 2,4'-dihydroxydiphenylsulfone, which is isolated. The method of isolating 2,4'-dihydroxydiphenylsulfone is not particularly limited. For example, 2,4'-dihydroxydiphenylsulfone may be isolated by neutralizing the dialkali metal salt directly with an acid, or the dialkali metal salt is converted into a monoalkali metal salt, which is isolated and subsequently neutralized to obtain 2,4'-dihydroxydiphenylsulfone. When the neutralization with an acid is conducted, water or an aqueous mixed solvent containing water and an organic solvent can be used as the solvent.

In the process of the present invention, by adjusting pH of water or an aqueous mixed solvent in which a dialkali metal salt of 2,4'-dihydroxydiphenylsulfone is dissolved to 4 to 6, the dialkali metal salt of 2,4'-dihydroxydiphenylsulfone can be converted into 2,4'-dihydroxy-diphenylsulfone, which is precipitated from the solution. It is generally not necessary that pH of the solvent is adjusted to less than 4 because, when pH of water or the aqueous mixed solvent is adjusted to 4, the dialkali metal salt of 2,4'-dihydroxydiphenylsulfone dissolved in the solvent is converted into 2,4'-dihydroxydiphenylsulfone, which is precipitated from the solution. When pH of water or the aqueous mixed solvent is higher than 6, there is the possibility that a monoalkali metal salt of 2,4'-dihydroxydiphenylsulfone is mixed with 2,4'-dihydroxydiphenylsulfone to cause decrease in the purity.

In the process of the present invention, a monoalkali metal salt of 2,4'-dihydroxydiphenylsulfone is formed by adjusting pH of water or an aqueous mixed solvent in which the dialkali metal salt of 2,4'-dihydroxydiphenylsulfone is dissolved to 6 to 10.5. The resultant monoalkali metal salt can be isolated and then dissolved again in water or an aqueous mixed solvent. By adjusting pH of the resultant aqueous solution to 4 to 6 with addition of an acid, the monoalkali metal salt can be converted into 2,4'-dihydroxydiphenylsulfone.

The aqueous mixed solvent used in the process of the present invention is not particularly limited, and a mixed solvent containing water and an alcohol can preferably be used. Examples of the alcohol used include methanol, ethanol, 1-propanol, 2-propanol, 2-methoxyethanol, 2-ethoxyethanol, 2-isopropoxyethanol, 2-butoxyethanol, and the like. Among these alcohols, aliphatic alcohols having 1 to 3 carbon atoms are preferably used, and methanol, ethanol, and 2-propanol are particularly preferably used. When an alcohol having 4 or more carbon atoms is used, there is the possibility that phase separation takes place in the mixed aqueous solution in which the dihydroxydiphenylsulfones or salts thereof are present.

In the process of the present invention, the purity of 2,4'-dihydroxydiphenylsulfone can be further increased by adding an aliphatic alcohol to a solution of a dialkali metal salt of 2,4'-dihydroxydiphenylsulfone in water to form an aqueous mixed solution, and subsequently by neutralizing the resultant aqueous mixed solution with an acid. The composition of the aqueous mixed solvent is not particularly limited, and an aqueous mixed solvent containing 60 to 90% by weight of water and 40 to 10% by weight of an aliphatic alcohol is preferable. When the content of an aliphatic alcohol is less than 10% by weight, there is the possibility that the effect of the aliphatic alcohol is not sufficiently exhibited. When the content of an aliphatic alcohol is more than 40% by weight, there is the possibility that the purity of the resultant 2,4'-dihydroxydiphenylsulfone decreases.

In the process of the present invention, 2,4'-dihydroxydiphenylsulfone obtained by neutralizing the solution with an acid can be further purified by recrystallization. As the solvent of recrystallization, an aqueous mixed solvent is preferably used, and a mixed solvent containing water and an alcohol is particularly preferably used. Examples of the alcohol include methanol, ethanol, 1-propanol, 2-propanol, 2-methoxyethanol, 2-ethoxyethanol, 2-isopropoxyethanol, 2-butoxyethanol, and the like. Among these alcohols, methanol, ethanol, and 2-propanol are preferably used.

To summarize the advantage obtained by the present invention, a high purity 2,4'-dihydroxydiphenylsulfone having a purity of 95 to 99.5% by weight can be obtained easily with a high yield from a mixture of isomers of dihydroxydiphenylsulfone containing 15% by weight or more of 2,4'-dihydroxydiphenylsulfone.

EXAMPLES

The invention will be understood more readily with reference to the following examples; however, these examples are intended to illustrate the invention and are not to be construed to limit the scope of the invention.

The contents of 2,4'-dihydroxydiphenylsulfone and 4,4'-dihydroxydiphenylsulfone were obtained by the quantitative analysis using high performance liquid chromatography.

Reaction Example 1 (Preparation of a crude product of dihydroxydiphenylsulfone)

A reactor was charged with 793 g of phenol, 334 g of sulfuric acid, and 16.5 g of phosphonic acid, and the dehydration reaction was allowed to proceed under a reduced pressure of 560 to 260 mm Hg at 150° to 165° C. for 3 hours. When 250 g of a mixture of phenol and water had been removed by distillation, 165 g of phenol was added to the reaction system, and the reaction was allowed to continue under a reduced pressure of 260 to 100 mm Hg for further 2 hours. When the amount of the distilled mixture of phenol and water reached 430 g, 165 g of phenol was further added, and the reaction was allowed to continue under a reduced pressure of 260 to 100 mm Hg for further 2 hours. When the amount of the distilled mixture of water and phenol finally reached 570 g, the reaction was finished, and 724 g of a crude product of dihydroxydiphenylsulfone containing 49% by weight of 2,4'-dihydroxydiphenylsulfone, 50% by weight of 4,4'-dihydroxydiphenylsulfone, and 1% by weight of other impurities was obtained. The yield was 85%.

Reaction Example 2 (Preparation of a crude product of dihydroxydiphenylsulfone)

A reactor was charged with 564 g of phenol and 300 g of sulfuric acid, and the dehydration reaction was allowed to proceed under a reduced pressure of 720 to 120 mm Hg at 140° to 155° C. for 5 hours. When 145 g of a mixture of phenol and water had been removed by distillation, 60 g of phenol was added to the reaction system, and the reaction was allowed to continue under a reduced pressure of 720 to 80 mm Hg for further 2 hours. When the amount of the distilled mixture of water and phenol finally reached 200 g, the reaction was finished, and 574 g of a crude product of dihydroxydiphenylsulfone containing 20% by weight of 2,4'-dihydroxydiphenylsulfone, 79% by weight of 4,4'-dihydroxydiphenylsulfone, and 1% by weight of other impurities was obtained. The yield was 75%.

Example 1

The crude product of dihydroxydiphenylsulfone obtained in Reaction Example 1 in an amount of 100 g (0.4 mol) was added to an aqueous solution prepared by dissolving 32 g (0.8 mol) of sodium hydroxide into 100 g of water, and the mixture was heated under refluxing. After the crude product of dihydroxydiphenylsulfone was completely dissolved, 10 g (0.1 mol) of sulfuric acid was added to the solution, and the solution was allowed to cool to 50° C. Monosodium salt of 4,4'-dihydroxydiphenylsulfone which was precipitated from the solution was removed by filtration. After the filtrate was cooled to a room temperature, pH of the solution was adjusted to 5.0 by adding sulfuric acid. The formed precipitate was separated by filtration and dried to obtain 49 g of a crystal. The obtained crystal contained 88% by weight of 2,4'-dihydroxydiphenylsulfone. The crystal in an amount of 40 g was dissolved in 160 g of a 30% by weight aqueous solution of methanol and recrystallized to obtain 36 g of 2,4'-dihydroxydiphenylsulfone as a precipitate. The purity of the obtained 2,4'-dihydroxydiphenylsulfone was 97% by weight.

Example 2

The crude product of dihydroxydiphenylsulfone obtained in Reaction Example 1 in an amount of 100 g (0.4 mol) was added to an aqueous solution prepared by dissolving 32 g (0.8 mol) of sodium hydroxide into 100 g of water, and the mixture was heated under refluxing. After the crude product of dihydroxydiphenylsulfone was completely dissolved, 10 g (0.1 mol) of sulfuric acid was added to the solution, and the solution was allowed to cool to 50° C. Monosodium salt of 4,4'-dihydroxydiphenylsulfone which was precipitated from the solution was removed by filtration. After the filtrate was cooled to a room temperature, 43 g of methanol was added to the filtrate to convert the solvent into a 30% by weight aqueous solution of methanol, pH of the solution was adjusted to 5.0 by adding sulfuric acid, and 38 g of 2,4'-dihydroxydiphenylsulfone was obtained as a precipitate. The purity of the obtained 2,4'-dihydroxydiphenylsulfone was 98% by weight.

Example 3

The crude product of dihydroxydiphenylsulfone obtained in Reaction Example 1 in an amount of 100 g (0.4 mol) was added to an aqueous solution prepared by dissolving 32 g (0.8 mol) of sodium hydroxide into 100 g of water, and the mixture was heated under refluxing. After the crude product of dihydroxydiphenylsulfone was completely dissolved, 10 g (0.1 mol) of sulfuric acid was added to the solution, and the solution was allowed to cool to 50° C. Monosodium salt of 4,4'-dihydroxydiphenylsulfone which was precipitated from the solution was removed by filtration. After the filtrate was cooled to a room temperature, sulfuric acid was added to the filtrate until pH of the filtrate became 9.5 to obtain 43 g of monosodium salt of 2,4'-dihydroxydiphenylsulfone as a precipitate. The purity of the obtained monosodium salt of 2,4'-dihydroxydiphenylsulfone was 99.2% by weight. The monosodium salt of 2,4'-dihydroxydiphenylsulfone was dissolved in 200 g of water by heating to 70° C., and sulfuric acid was added to the resultant solution until pH of the solution became 5.0 to obtain 39 g of 2,4'-dihydroxydiphenylsulfone as a precipitate. The purity of the obtained 2,4'-dihydroxydiphenylsulfone-was 99.5% by weight.

Example 4

The crude product of dihydroxydiphenylsulfone obtained in Reaction Example 1 in an amount of 100 g (0.4 mol) was added to an aqueous solution prepared by dissolving 24 g (0.6 mol) of sodium hydroxide into 100 g of water, and the mixture was heated under refluxing. After the crude product of dihydroxydiphenylsulfone was completely dissolved, 15 g of sodium sulfate was added to the solution, and the solution was allowed to cool to 50° C. Monosodium salt of 4,4'-dihydroxydiphenylsulfone which was precipitated from the solution was removed by filtration. After the filtrate was cooled to a room temperature, sulfuric acid was added to the filtrate until pH of the filtrate became 5.0 to obtain 46 g of a crystal as a precipitate. The obtained crystal contained 86% by weight of 2,4'-dihydroxydiphenylsulfone. The crystal in an amount of 40 g was dissolved in 160 g of a 30% by weight aqueous solution of 2-propanol and recrystallized to obtain 35 g of 2,4'-dihydroxydiphenylsulfone as a precipitate. The purity of the obtained 2,4'-dihydroxydiphenylsulfone was 97% by weight.

Example 5

The crude product of dihydroxydiphenylsulfone obtained in Reaction Example 2 in an amount of 200 g (0.8 mol) was added to an aqueous solution prepared by dissolving 68 g (1.7 mol) of sodium hydroxide into 300 g of water, and the mixture was heated under refluxing. After the crude product of dihydroxydiphenylsulfone was completely dissolved, 36 g (0.37 mol) of sulfuric acid was added to the solution, and the solution was allowed to cool to 40° C. Monosodium salt of 4,4'-dihydroxydiphenylsulfone which was precipitated from the solution was removed by filtration. After the filtrate was cooled to a room temperature, sulfuric acid was added to the filtrate to adjust pH of the filtrate to 8.5. The formed precipitate was separated by filtration and dried to obtain 40 g of a crystal. The obtained crystal contained 90% by weight of monosodium salt of 2,4'-dihydroxydiphenylsulfone. The crystal was dissolved in 160 g of a 30% by weight aqueous solution of methanol, and sulfuric acid was added to the solution until pH of the solution became 5.0 to obtain 32 g of 2,4'-dihydroxydiphenylsulfone as a precipitate. The purity of the obtained 2,4'-dihydroxydiphenylsulfone was 99.5% by weight.

Comparative Example 1

The crude product of dihydroxydiphenylsulfone obtained in Reaction Example 1 in an amount of 100 g (0.4 mol) was added to an aqueous solution prepared by dissolving 16 g (0.4 mol) of sodium hydroxide into 300 g of water, and the mixture was heated under refluxing. After the crude product of dihydroxydiphenylsulfone was completely dissolved, 10 g (0.1 mol) of sulfuric acid was added to the solution, and the solution was allowed to cool to 50° C. Monosodium salt of 4,4'-dihydroxydiphenylsulfone which was precipitated from the solution was removed by filtration. After the filtrate was cooled to a room temperature, sulfuric acid was added to the filtrate until pH of the solution became 5.0 to obtain 20 g of a crystal as a precipitate. The obtained crystal contained 51% by weight of 2,4'-dihydroxydiphenylsulfone. The crystal was dissolved in 80 g of a 30% by weight aqueous solution of methanol and recrystallized to obtain 13 g of a crystal as a precipitate. The crystal obtained after the recrystallization contained 52 % by weight of 2,4'-dihydroxydiphenylsulfone.

Comparative Example 2

The crude product of dihydroxydiphenylsulfone obtained in Reaction Example 2 in an amount of 200 g (0.8 mol) was added to an aqueous solution prepared by dissolving 32 g (0.8 mol) of sodium hydroxide into 600 g of water, and the mixture was heated under refluxing. After the crude product of dihydroxydiphenylsulfone was completely dissolved, 30 g of sodium sulfate was added to the solution, and the solution was allowed to cool to 50° C. Monosodium salt of 4,4'-dihydroxydiphenylsulfone which was precipitated from the solution was removed by filtration. After the filtrate was cooled to a room temperature, sulfuric acid was added to the filtrate until pH of the solution became 7.5 to obtain 24 g of a crystal as a precipitate. The obtained crystal contained 49% by weight of monosodium salt of 2,4'-dihydroxydiphenylsulfone. The crystal was dissolved in 100 g of a 30% by weight aqueous solution of methanol. Sulfuric acid was added to this solution until pH of the solution became 5.0 to obtain 13 g of a crystal as a precipitate. The obtained crystal contained 50% by weight of 2,4'-dihydroxydiphenylsulfone.

Reaction Example 3 (Preparation of a crude product of dihydroxydiphenylsulfone)

A reactor was charged with 564 g of phenol and 300 g of sulfuric acid, and the dehydration reaction was allowed to proceed under a reduced pressure of 720 to 120 mm Hg at 140° to 150° C. for 5 hours. When 145 g of a mixture of phenol and water had been removed by distillation, 80 g of phenol was added to the reaction system, and the reaction was allowed to continue under a reduced pressure of 720 to 80 mm Hg for further 4 hours. When the amount of the distilled mixture of phenol and water finally reached 220 g, the reaction was finished, and 651 g of a crude product of dihydroxydiphenylsulfone containing 10% by weight of 2,4'-dihydroxydiphenylsulfone, 88% by weight of 4,4'-dihydroxydiphenylsulfone, and 2% by weight of other impurities was obtained. The yield was 85%.

Comparative Example 3

The crude product of dihydroxydiphenylsulfone obtained in Reaction Example 3 in an amount of 200 g (0.8 mol) was added to an aqueous solution prepared by dissolving 64 g (1.6 mol) of sodium hydroxide into 300 g of water, and the mixture was heated under refluxing. After the crude product of dihydroxydiphenylsulfone was completely dissolved, 34 g (0.35 mol) of sulfuric acid was added to the solution, and the solution was allowed to cool to 50° C. Monosodium salt of 4,4'-dihydroxydiphenylsulfone which was precipitated from the solution was removed by filtration. After the filtrate was cooled to a room temperature, sulfuric acid was added to the filtrate until pH of the solution became 5.0 to obtain 28 g of a crystal as a precipitate. The obtained crystal contained 60% by weight of 2,4'-dihydroxydiphenylsulfone. The crystal was dissolved in 84 g of a 30% by weight aqueous solution of methanol and recrystallized to obtain 14 g of a crystal as a precipitate. The crystal obtained after the recrystallization contained 79% by weight of 2,4'-dihydroxydiphenylsulfone.

What is claimed is:

1. A process for producing a high purity 2,4'-dihydroxydiphenylsulfone comprising separating 2,4'-dihydroxydiphenylsulfone from 4,4'-dihydroxydiphenylsulfone by adding a hydroxide of an alkali metal in an amount which is the total of an amount by mol 1.6 to 2.2 times as great as the amount by mol of 2,4'-dihydroxydiphenylsulfone and an amount by mol 0.8 to 1.2 times as great as the amount by mol of 4,4'-dihydroxydiphenylsulfone to a solution of a mixture of 2,4'-dihydroxydiphenylsulfone and 4,4'-dihydroxydiphenylsulfone containing at least 15% by weight of 2,4'-dihydroxydiphenylsulfone, based on the mixtures, in water, to allow 2,4'-dihydroxydiphenylsulfone to remain dissolved in water in the form of a dialkali metal salt thereof and 4,4'-dihydroxydiphenylsulfone to be precipitated from the solution in the form of a monoalkali metal salt thereof.

2. A process for producing a high purity 2,4'-dihydroxydiphenylsulfone comprising separating 2,4'-dihydroxydiphenylsulfone from 4,4'-dihydroxydiphenylsulfone by adding a hydroxide of an alkali metal in an amount which is the total of an amount by mol 1.6 to 2.2 times as great as the amount by mol of 2,4'-dihydroxydiphenylsulfone and an amount by mol 1.6 to 2.4 times as great as the amount by mol of 4,4'-dihydroxydiphenylsulfone to a solution of a mixture of 2,4'-dihydroxydiphenylsulfone and 4,4'-dihydroxydiphenylsulfone containing at least 15% by weight of 2,4'-dihydroxydiphenylsulfone, based on the mixture, in water, and by subsequently adding an acid in an amount by mol corresponding to an amount by mol of the hydroxide of an alkali metal which is 0.8 to 1.2 times as the amount by mol of 4,4'-dihydroxydiphenylsulfone to the resultant solution to neutralize the alkali metal.

3. A process for producing a high purity 2,4'-dihydroxydiphenylsulfone comprising separating 2,4'-dihydroxydiphenylsulfone from 4,4'-dihydroxydiphenylsulfone by adding a carbonate of an alkali metal in an amount which is the total of an amount by mol 0.8 to 1.1 times as great as the amount by mol of 2,4'-dihydroxydiphenylsulfone and an amount by mol 0.4 to 0.6 times as great as the amount by mol of 4,4'-dihydroxydiphenylsulfone to a solution of a mixture of 2,4'-dihydroxydiphenylsulfone and 4,4'-dihydroxydiphenylsulfone containing at least 15% by weight of 2,4'-dihydroxydiphenylsulfone, based on the mixture, in water, to allow 2,4'-dihydroxydiphenylsulfone to remain dissolved in water in the form of a dialkali metal salt thereof and 4,4'-dihydroxydiphenylsulfone to be precipitated from the solution in the form of a monoalkali metal salt thereof.

4. A process for producing a high purity 2,4'-dihydroxydiphenylsulfone, comprising separating 2,4'-dihydroxydiphenylsulfone from 4,4'-dihydroxydiphenylsulfone by adding a carbonate of an alkali metal in an amount which is the total of an amount by mol 0.8 to 1.1 times as great as the amount by mol of 2,4'-dihydroxydiphenylsulfone and an amount by mol 0.8 to 1.2 times as great as the amount by mol of 4,4'-dihydroxydiphenylsulfone to a solution of a mixture of 2,4'-dihydroxydiphenylsulfone and 4,4'-dihydroxydiphenylsulfone containing at least 15% by weight of 2,4'-dihydroxydiphenylsulfone, based on the mixture, in water, and by subsequently adding an acid in an amount by mol corresponding to an amount by mol of the carbonate of an alkali metal which is 0.4 to 0.6 times as great as the amount by mol of 4,4'-dihydroxydiphenylsulfone to the resultant solution to neutralize the alkali metal.

5. A process for producing a high purity 2,4'-dihydroxydiphenylsulfone according to claim 1, wherein the monoalkali metal salt of 4,4'-dihydroxydiphenylsulfone which is precipitated from the solution is removed by filtration at 20° to 70° C.

6. A process for producing a high purity 2,4'-dihydroxydiphenylsulfone according to claim 2, wherein the monoalkali metal salt of 4,4'-dihydroxydiphenylsulfone which is precipitated from the solution is removed by filtration at 20° to 70° C.

7. A process for producing a high purity 2,4'-dihydroxydiphenylsulfone according to claim 3, wherein the monoalkali metal salt of 4,4'-dihydroxydiphenylsulfone which is precipitated from the solution is removed by filtration at 20° to 70° C.

8. A process for producing a high purity 2,4'-dihydroxydiphenylsulfone according to claim 4, wherein the monoalkali metal salt of 4,4'-dihydroxydiphenylsulfone which is precipitated from the solution is removed by filtration at 20° to 70° C.

9. A process for producing a high purity 2,4'-dihydroxydiphenylsulfone according to claim 5, wherein 2,4'-dihydroxydiphenylsulfone is precipitated from a filtrate obtained by the filtration by adjusting pH of the filtrate to 4 to 6 with addition of an acid.

10. A process for producing a high purity 2,4'-dihydroxydiphenylsulfone according to claim 6, wherein 2,4'-dihydroxydiphenylsulfone is precipitated from a filtrate obtained by the filtration by adjusting pH of the filtrate to 4 to 6 with addition of an acid.

11. A process for producing a high purity 2,4'-dihydroxydiphenylsulfone according to claim 7, wherein 2,4'-dihydroxydiphenylsulfone is precipitated from a filtrate obtained by the filtration by adjusting pH of the filtrate to 4 to 6 with addition of an acid.

12. A process for producing a high purity 2,4'-dihydroxydiphenylsulfone according to claim 8, wherein 2,4'-dihydroxydiphenylsulfone is precipitated from a filtrate obtained by the filtration by adjusting pH of the filtrate to 4 to 6 with addition of an acid.

13. A process for producing a high purity 2,4'-dihydroxydiphenylsulfone according to claim 5, wherein a monoalkali metal salt of 2,4'-dihydroxydiphenylsulfone is precipitated from a filtrate obtained by the filtration by adjusting pH of the filtrate to 6 to 10.5, isolated, and subsequently dissolved in an aqueous solvent, and 2,4'-dihydroxydiphenylsulfone is precipitated from the resultant aqueous solution by adjusting pH of the aqueous solution to 4 to 6 with addition of an acid.

14. A process for producing a high purity 2,4'-dihydroxydiphenylsulfone according to claim 6, wherein a monoalkali metal salt of 2,4'-dihydroxydiphenylsulfone is precipitated from a filtrate obtained by the filtration by adjusting pH of the filtrate to 6 to 10.5, isolated, and subsequently dissolved in an aqueous solvent, and 2,4'-dihydroxydiphenylsulfone is precipitated from the resultant aqueous solution by adjusting pH of the aqueous solution to 4 to 6 with addition of an acid.

15. A process for producing a high purity 2,4'-dihydroxydiphenylsulfone according to claim 7, wherein a monoalkali metal salt of 2,4'-dihydroxydiphenylsulfone is precipitated from a filtrate obtained by the filtration by adjusting pH of the filtrate to 6 to 10.5, isolated, and subsequently dissolved in an aqueous solvent, and 2,4'-dihydroxydiphenylsulfone is precipitated from the resultant aqueous solution by adjusting pH of the aqueous solution to 4 to 6 with addition of an acid.

16. A process for producing a high purity 2,4'-dihydroxydiphenylsulfone according to claim 8, wherein a monoalkali metal salt of 2,4'-dihydroxydiphenylsulfone is precipitated from a filtrate obtained by the filtration by adjusting pH of the filtrate to 6 to 10.5, isolated, and subsequently dissolved in an aqueous solvent, and 2,4'-dihydroxydiphenylsulfone is precipitated from the resultant aqueous solution by adjusting pH of the aqueous solution to 4 to 6 with addition of an acid.

17. A process for producing a high purity 2,4'-dihydroxydiphenylsulfone according to claim 5, wherein an aliphatic alcohol having 1 to 3 carbon atoms is added to a filtrate obtained by the filtration in such an amount that the resultant mixed solvent contains 60 to 90% by weight of water and 40 to 10% by weight of the aliphatic alcohol, and 2,4'-dihydroxydiphenylsulfone is precipitated from the resultant solution by adjusting pH of the solution to 4 to 6 with addition of an acid.

18. A process for producing a high purity 2,4'-dihydroxydiphenylsulfone according to claim 6, wherein an aliphatic alcohol having 1 to 3 carbon atoms is added to a filtrate obtained by the filtration in such an amount that the resultant mixed solvent contains 60 to 90% by weight of water and 40 to 10% by weight of the aliphatic alcohol, and 2,4'-dihydroxydiphenylsulfone is precipitated from the resultant solution by adjusting pH of the solution to 4 to 6 with addition of an acid.

19. A process for producing a high purity 2,4'-dihydroxydiphenylsulfone according to claim 7, wherein an aliphatic alcohol having 1 to 3 carbon atoms is added to a filtrate obtained by the filtration in such an amount that the resultant mixed solvent contains 60 to 90% by weight of water and 40 to 10% by weight of the aliphatic alcohol, and 2,4'-dihydroxydiphenylsulfone is precipitated from the resultant solution by adjusting pH of the solution to 4 to 6 with addition of an acid.

20. A process for producing a high purity 2,4'-dihydroxydiphenylsulfone according to claim 8, wherein an aliphatic alcohol having 1 to 3 carbon atoms is added to a filtrate obtained by the filtration in such an amount that the resultant mixed solvent contains 60 to 90% by weight of water and 40 to 10% by weight of the aliphatic alcohol, and 2,4'-dihydroxydiphenylsulfone is precipitated from the resultant solution by adjusting pH of the solution to 4 to 6 with addition of an acid.

* * * * *